United States Patent [19]

Härtl

[11] Patent Number: 4,587,993
[45] Date of Patent: May 13, 1986

[54] HIGH-PRESSURE VISCOUS DAMPER

[75] Inventor: Hans-Georg Härtl, Waldbronn, Fed. Rep. of Germany

[73] Assignee: Hewlett-Packard GmbH, Boeblingen, Fed. Rep. of Germany

[21] Appl. No.: 742,632

[22] Filed: Jun. 6, 1985

Related U.S. Application Data

[63] Continuation of Ser. No. 580,572, Feb. 15, 1984, abandoned.

[30] Foreign Application Priority Data

Feb. 25, 1983 [DE] Fed. Rep. of Germany ....... 3306631

[51] Int. Cl.$^4$ ............................................. F16L 55/04
[52] U.S. Cl. .................................. 138/30; 210/198.2
[58] Field of Search ............................ 138/30; 73/707; 210/198.2, 349; 220/85 B; 417/540

[56] References Cited

U.S. PATENT DOCUMENTS

| 2,904,077 | 9/1959 | Trumper | 138/30 |
| 2,916,052 | 12/1959 | Peters | 138/30 |
| 3,033,552 | 5/1962 | Ogden | 138/30 X |
| 3,061,039 | 10/1962 | Peters | 138/30 X |
| 4,166,655 | 9/1979 | Spero | 138/30 X |
| 4,222,414 | 9/1980 | Achener | 138/30 |
| 4,234,427 | 11/1980 | Boehme | 138/30 X |
| 4,305,428 | 12/1981 | Burton | 138/30 |
| 4,367,786 | 1/1983 | Häfner et al. | 138/30 X |
| 4,427,029 | 1/1984 | Chorney | 138/30 |

FOREIGN PATENT DOCUMENTS 2020249 11/1971 Fed. Rep. of Germany.

Primary Examiner—James E. Bryant, III
Attorney, Agent, or Firm—Jeffery B. Fromm

[57] ABSTRACT

A high-pressure viscous damper is proposed, in particular for use in liquid chromatographs, in which two chambers are separated by an elastic partition, and the one chamber receives a fluid to be damped and the other chamber holds a damping fluid. In the chamber holding the damping fluid an insert is provided within the fluid with a selected volume and temperature expansion coefficient so that by the combination of the insert and damping fluid and the volume and wall material of the second chamber a volume compensation is achieved.

10 Claims, 1 Drawing Figure

U.S. Patent     May 13, 1986     4,587,993
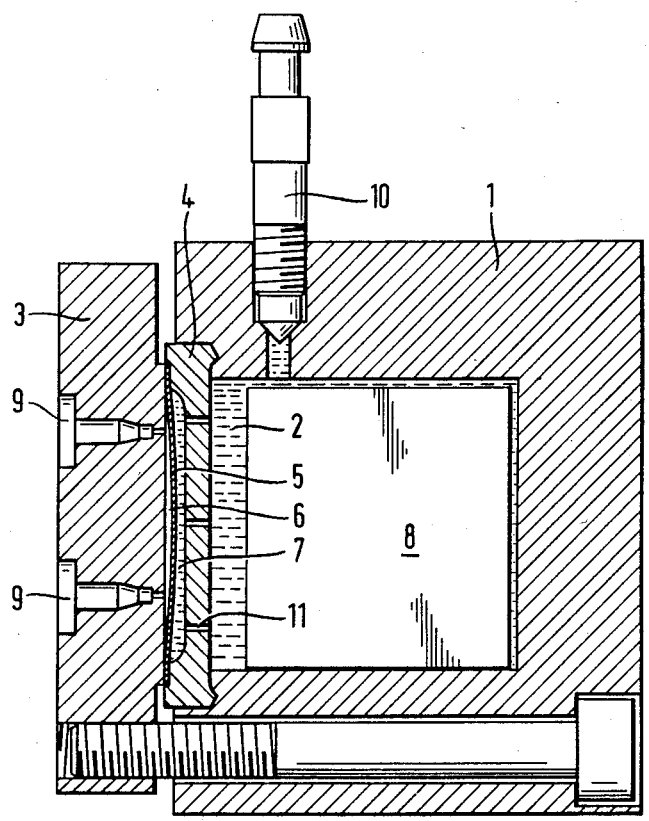

HIGH-PRESSURE VISCOUS DAMPER

CROSS REFERENCE TO RELATED APPLICATION

This application is a continuation of application Ser. No. 580,572, filed 2/15/84, now abandoned.

BACKGROUND OF THE INVENTION

The invention relates to high-pressure viscous dampers. Viscous dampers serve to absorb short-term feed variations in fluid systems in order to avoid undesired excessive pressure rises and to average a pulsating feed of fluid. To this end, known viscous dampers are constructed with first and second chambers separated by an elastic partition or membrane, one chamber receiving the fluid to be damped with respect to pressure and flow variations and the second chamber holding a damping fluid. A temporarily increased feed of fluid results in a pressure rise which is absorbed by the damping fluid via the elastic partition. If less fluid is conveyed temporarily, the pressure sinks and the damping fluid expands and compensates for the lacking volume.

In liquid chromatographs viscous dampers serve to equalize the flow of a solvent through a separating column, because flow variations affect the measuring accuracy disadvantageously. Moreover, it is extremely important that the chambers through which the solvent flows have a dead volume as small and constant as possible. For example, at a feed rate of one hundred microliters per minute which at today's standards is not unusual for the achievement of high sensitivity, a few microliters of dead volume have an extremely negative effect.

The known high-pressure viscous dampers do, however, have the disadvantage that their dead volume changes with temperature. Because of the different temperature expansion coefficients and because of the materials involved, a temperature change leads to a change in pressure with an accompanying change in volume of the second chamber by deformation of the elastic partition. Consequently, the dead volume represented by the first chamber also changes. Particularly the known fluids which are sufficiently compressible for damping purposes (e.g. Hexane) have a substantially higher temperature expansion coefficient than the metals used for the housing of such dampers (e.g. steel).

In the known high-pressure viscous dampers, the damping fluid is therefore filled into the housing at a relatively high temperature of approximately 40 degrees centigrade and this temperature is maintained during operation by way of thermostats. This leads to quite substantial problems regarding temperature sensitivity of some solvents, and the regulation of temperature requires some additional expenditure.

SUMMARY OF THE INVENTION

The present invention provides an improved high-pressure viscous damper in which variations of the operating temperature have minimal effect upon the volume available for holding the fluid to be damped.

The illustrated embodiment of the invention includes in a high-pressure viscouse damper having two chambers separated by an elastic partition with the first chamber receiving the fluid to be damped and the second chamber holding a damping fluid, an insert filling a portion of the volume of the second chamber which has a predetermined volume and temperature expansion coefficient relative to the volume of the second chamber, the temperature expansion coefficient of the material of the walls of the second chamber, the volume of the damping fluid and the temperature expansion coefficient of the damping fluid.

For satisfactory damping action, the materials of the chamber walls, the compressible fluid and the insert are selected relative to the volumes of the second chamber and the insert so that the volume of the first chamber is nearly constant throughout the required operating range of 0 to 55 degrees centigrade. The selection of the materials and volumes is based upon the basic functionality of the physical properties of the materials, namely: (a) that the compressibility of a material multiplied by its volume determines the damping characteristic; and (b) that the heat expansion of the material multiplied by its volume is the decisive factor for the volume compensation needed.

BRIEF DESCRIPTION OF THE DRAWING

The single FIGURE in the drawing is a cross-sectional view of one embodiment of the invention.

DESCRIPTION OF THE PREFERRED EMBODIMENTS

Referring now to the FIGURE, in a housing 1 a space 2 is provided which is closed by a lid 3. Between housing 1 and lid 3 a plate-shaped insert 4 as well as a membrane 5 are restrained and clamped between lid 3 and housing 1 by way of bolts fixing the lid to the housing. Two chambers 6 and 7, separated by the membrane, result between the lid 3 and the plate-shaped insert 4. In space 2 of the housing 1 an insert is disposed which occupies the major volume of the space 2.

In cover 3, two outlets 9 are provided for directing the fluid to be damped through chamber 6. If the illustrated example is to serve as a high-pressure viscous damper in a liquid chromatograph, this fluid will be the solvent flowing to the column.

By way of a filling nipple 10 space 2 is filled with water to which an antifreeze agent has been added. In insert 4, bores 11 are provided for connecting space 2 with the chamber 7, so that in chamber 7 the water is at the same pressure as in space 2. Thus, the solvent is separated from the water by way of membrane 5.

By selecting appropriate materials and volumes for the housing 1 and insert 8 and using water, it is accomplished that the position of the separating membrane remains constant, independently from temperature. Using water as the damping fluid, the compensation may be achieved, for example, with a housing consisting of aluminium and an insert 8 made from lithium-aluminium silicate. Accompanying the temperature-dependent expansion of the water and insert 8, a corresponding expansion of the housing 1 and thus the space 2 occurs. In the temperature range between 0 to 55 degrees centigrade required for some liquid chromatographs, the material and volume combination results in a constant membrane position so that the membrane at pressure changes within the solvent 6 can move accordingly in the direction toward chamber 7 in independence from temperature, which leads to an equal counter pressure in chamber 7 with accompanying damping action.

Since a small dead volume is preferable to overpressure, and the expansion characteristic over the temperature range are merely similar but not equal to a linear compensation line, space 2 is filled at a temperature of 55 degrees centigrade and allowed to cool down to the operating temperature.

For temperature compensation the function $$V_C \times_m = V_f \times_f + V_i \times_i$$

applies, wherein c stands for chamber, m for wall material, f for compressible fluid and i for insert. From this function the volume of the second chamber and the insert can be determined in relation to the properties of the selected materials to be used.

This makes it possible to advantageously achieve a full compensation of the temperature expansions, and thereby a constant volume of the solvent chamber.

For example, the fluid can have a very small or even a negative temperature expansion coefficient. By choosing a material with a particularly large temperature expansion coefficient such as aluminum for the chamber walls it is possible to achieve a relatively large increase of the volume of the second chamber with temperature. While steel has a temperature coefficient of $=3 \times 10^{-5}$, aluminum has a of $7 \times 10^{-5}$ which is more than twice the value of steel. Then, an insert having a temperature expansion coefficient near zero may be chosen with an appropriate volume in such a way that the expansion of the second chamber is sufficient to accomodate the combined expansion of the damping fluid and insert. This is the volume compensation required.

The damping fluid used may be water. Because in water the ratio between temperature expansion and compressibility is favorable (small), it is an almost optimal damping fluid which allows for a small physical size of the high-pressure damper. For storage compatibility of $-40$ degrees centigrade, the water can be supplemented by an antifreeze agent which, as is commonly known in the field, does not deteriorate the damping characteristics.

A particularly advantageous material for the insert is a lithium-aluminum silicate with a temperature expansion coefficient of 0 to $0.6 \times 10^{-6}$. For a very small temperature coefficient, also quartz glass proves suitable. If need be, glass ceramic materials which have a negative temperature expansion coefficient can also be utilized.

I claim:

1. A high pressure viscous damper for damping pressure and flow variations in a fluid, particularly for use in a liquid chromatograph, comprising:
   a first chamber adapted to receive a fluid to be damped;
   a closed second chamber holding a damping liquid;
   an elastic partition separating the first chamber from the second chamber; and
   an insert filling a substantial portion of the volume of the second chamber and the remaining portion of the volume of the second chamber being substantially filled with the damping liquid so that substantially no gas is present within the second chamber, said insert having a predetermined volume and temperature expansion coefficient relative to the volume of the second chamber, the temperature expansion coefficient of the material of the walls of the second chamber, the volume of the damping liquid and the temperature expansion coefficient of the damping liquid to compensate the linear portions of the temperature-dependent volume variations of the second chamber and the damping liquid so that in the operating temperature range of the damper the position of the elastic partition remains substantially constant but can move in response to pressure changes independent of temperature.

2. A high-pressure viscous damper in accordance with claim 1, wherein the second chamber comprises a cup-shaped housing which is closed by means of a lid with at least one opening for the liquid to be damped and wherein said elastic partition is a membrane clamped between the lid and the housing.

3. A high-pressure viscous damper in accordance with claim 2, wherein said lid is disposed on one side of said membrane, and further including a plate-shaped insert disposed on the other side of said membrane and having openings for allowing passage of the damping liquid said lid and said plate-shaped insert being operative to limit deflection of the membrane in opposite directions.

4. A high-pressure viscous damper in accordance with claim 3, wherein the plate-shaped insert is clamped in a composite fashion with the membrane between the housing and the lid.

5. A high-pressure viscous damper in accordance with claim 1, wherein the damping liquid is water containing an antifreeze agent.

6. A high-pressure viscous damper in accordance with claim 1, wherein the walls of the second chamber consist of an aluminum alloy.

7. A high-pressure viscous damper in accordance with claim 1, wherein the insert consists of a lithium-aluminum-silicate.

8. A high-pressure viscous damper in accordance with claim 1, wherein the insert consists of quartz glass.

9. A high-pressure viscous damper in accordance with claim 1, wherein the insert consists of a material with a negative temperature expansion coefficient.

10. A high-pressure viscous damper in accordance with claim 9, wherein the insert consists of a glass ceramics material.

* * * * *